United States Patent
Yanagisawa

(10) Patent No.: US 9,596,844 B2
(45) Date of Patent: Mar. 21, 2017

(54) AGROCHEMICAL SOLID FORMULATION

(71) Applicant: Sumitomo Chemical Company, Limited, Tokyo (JP)

(72) Inventor: Kazuyuki Yanagisawa, Takarazuka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 14/770,279

(22) PCT Filed: Feb. 25, 2014

(86) PCT No.: PCT/JP2014/055202
§ 371 (c)(1),
(2) Date: Aug. 25, 2015

(87) PCT Pub. No.: WO2014/133179
PCT Pub. Date: Sep. 4, 2014

(65) Prior Publication Data
US 2016/0000069 A1    Jan. 7, 2016

(30) Foreign Application Priority Data

Feb. 28, 2013    (JP) .................................. 2013-038435

(51) Int. Cl.
*A01N 25/22*        (2006.01)
*A01N 47/16*        (2006.01)
*A01N 25/08*        (2006.01)

(52) U.S. Cl.
CPC ............ *A01N 25/22* (2013.01); *A01N 25/08* (2013.01); *A01N 47/16* (2013.01)

(58) Field of Classification Search
CPC ...................................................... A01N 25/22
See application file for complete search history.

(56) References Cited

U.S. PATENT DOCUMENTS

| | | | |
|---|---|---|---|
| 2006/0089315 A1* | 4/2006 | Otsubo | A01N 43/56 514/22 |
| 2013/0324488 A1 | 12/2013 | Stark et al. | |
| 2014/0128411 A1 | 5/2014 | Ogawa et al. | |

FOREIGN PATENT DOCUMENTS

| | | | |
|---|---|---|---|
| CN | 102919255 A | 2/2013 | |
| JP | 2002316902 A | 10/2002 | |
| JP | 2006249067 A | 9/2006 | |
| JP | 2010189354 A | 9/2010 | |
| JP | 2012012299 A | 1/2012 | |
| JP | 5034142 B2 | 9/2012 | |
| JP | 2013231001 A | 11/2013 | |
| WO | 2012117060 A1 | 9/2012 | |
| WO | WO 2012121413 A1 * | 9/2012 | ............. A01N 25/04 |
| WO | 2013008604 A1 | 1/2013 | |
| WO | 2013162038 A | 10/2013 | |

OTHER PUBLICATIONS

Verdegaal Brothers, Inc. "Sulfuric Acid." © Jan. 13, 2012. Available from: < http://web.archive.org/web/20120113034135/http://www.verdegaalbrothers.com/acid.php >.*
Brunings, A., et al. "Are Phosphorous and Phosphoric Acids Equal Phosphorous Sources for Plant Growth?" © Jul. 7, 2013. Available from: < http://web.archive.org/web/20130707082653/http://edis.ifas.ufl.edu/hs254 >.*
Purdue University. "pH, pOH, pKa, and pKb". © Apr. 11, 2012. Available from: < http://web.archive.org/web/20120411023615/http://www.chem.purdue.edu/gchelp/howtosolveit/Equilibrium/Calculating_pHandpOH.htm >.*
International Search Report issued Apr. 8, 2014 in International Application No. PCT/JP2014/055202.
Supplementary European Search Report issued Jul. 21, 2016 in EP Application No. 14757774.6.
European Search Opinion issued Jul. 21, 2016 in EP Application No. 14757774.6.
Sumitomo Chemical, "Research and Development of a Novel Fungicide 'Fenpyrazamine'", pp. 1-14 (Jan. 2014).
Office Action issued Apr. 19, 2016 in CN Application No. 201480010194.1.
Office Action issued Nov. 9, 2016 in CN Application No. 201480010194.1.

\* cited by examiner

*Primary Examiner* — Noble Jarrell
*Assistant Examiner* — John S Kenyon
(74) *Attorney, Agent, or Firm* — Panitch Schwarze Belisario & Nadel LLP

(57) ABSTRACT

An agrochemical solid formulation contains fenpyrazamine and an acid component. The formulation has no problem of emission of odor and has excellent storage stability. A mixture of 1 g of the agrochemical solid formulation and 99 g of ion exchange water has a pH at 25° C. of 8 or less.

10 Claims, No Drawings

AGROCHEMICAL SOLID FORMULATION

CROSS-REFERENCE TO RELATED APPLICATION

This application is a Section 371 of International Application No. PCT/JP2014/055202, filed Feb. 25, 2014, which was published in the Japanese language on Sep. 4, 2014, under International Publication No. WO 2014/133179 A1, and the disclosure of which is incorporated herein by reference.

TECHNICAL FIELD

The present invention relates to an agrochemical solid formulation comprising fenpyrazamine.

BACKGROUND ART

Conventionally, an agrochemical formulation comprising fenpyrazamine has been known as an agricultural fungicide, and for example, a granular agrochemical composition comprising fenpyrazamine and lignin sulfonate is practically used (for example, see JP-A-2006-249067).

The formulation sometimes may emit an odor, for example, during storage or transportation under a high temperature, and the like. In most cases in which odors are emitted, they do not involve quality degradation causing a practical problem such as decomposition of agrochemical active ingredient. However, the odor may be recognized as an unpleasant odor, depending on the user and the use situation, thus it is desired to suppress the emission of odor.

An object of the present invention is to provide a fenpyrazamine-containing agrochemical solid formulation which has no problem of emission of odor and also has excellent stability in a practical situation.

DISCLOSURE OF THE INVENTION

The present inventors have studied to find a fenpyrazamine-containing agrochemical solid formulation which has no problem of emission of odor and also has excellent storage stability in a practical situation, and consequently achieved the present invention.

More specifically, the present invention is as described below.

[1] An agrochemical solid formulation comprising fenpyrazamine and an acid component, wherein the pH at 25° C. of a mixture of 1 g of the agrochemical solid formulation and 99 g of ion exchange water is 8 or less.
[2] The agrochemical solid formulation according to [1], wherein the acid component is at least one selected from the group consisting of phosphoric acid and sulfuric acid.
[3] The agrochemical solid formulation according to [1] or [2], wherein the pH is in the range of 3 to 6.
[4] The agrochemical solid formulation according to any of [1] to [3], further comprising lignin sulfonate.

According to the present invention, a fenpyrazamine-containing agrochemical solid formulation which has no problem of emission of odor and also has excellent stability in a practical situation, for example, an aqueous dispersion of the present solid formulation used when applying the present solid formulation to a plant and the like can be provided.

MODE FOR CARRYING OUT THE INVENTION

The agrochemical solid formulation of the present invention (hereinafter, referred to as the present solid formulation) comprises fenpyrazamine, in an amount of usually 5 to 90% by weight, and preferably 15 to 80% by weight, based on 100% by weight of the present solid formulation.

The present solid formulation is a formulation having a pH at 25° C. of a mixture of 1 g of the present solid formulation and 99 g of ion exchange water (hereinafter, referred to as pH of the present solid formulation) of 8 or less. The present solid formulation is a formulation having a pH of 8 or less, thereby exhibiting the effect of the present invention, and the pH of the present solid formulation is preferably in the range of 3 to 8, and more preferably in the range of 3 to 6. The ion exchange water in the present invention refers to water purified using a cation exchange resin and an anion exchange resin, and usually water having an electric conductivity at 25° C. of less than 0.1 mS/m.

In the present solid formulation, the pH at 25° C. is a pH value that is measured while a mixed liquid obtained by putting 1 g of the present solid formulation to 99 g of ion exchange water and sufficiently stirring the mixture using a magnetic stirrer or the like is maintained at 25° C. using a thermostat bath or the like, and a glass electrode of a glass electrode type pH meter is immersed in the mixed liquid, the pH value determined at a point where the change of the difference in 10 seconds is stabilized to within ±1 mV.

The present solid formulation comprises an acid component in an amount required for having a pH of 8 or less. The acid component includes inorganic acids, organic acids, and the like. The inorganic acids include hypochlorous acid, sulfuric acid, sulfurous acid, nitric acid, phosphoric acid, boric acid, and the like. The organic acids include saturated or unsaturated fatty acids such as acetic acid, propionic acid, butyric acid, octanoic acid, palmitic acid, oleic acid, stearic acid and HARTALL fatty acid (extract from timber composed mainly of oleic acid and linoleic acid, and also referred to as tall oil fatty acid: manufactured by Harima Chemicals Group, Inc.), aromatic carboxylic acids such as benzoic acid and phthalic acid, di- or tri-carboxylic acids such as succinic acid, malic acid, oxalic acid and citric acid, carboxylic acids such as sorbic acid and lactic acid, organic phosphoric acids such as C1 to C6 mono- or di-alkyl phosphates (for example, diisopropylphosphate, monoisopropylphosphate, PAP (mixture composed mainly of diisopropylphosphate and monoisopropylphosphate: manufactured by NIPPON CHEMICAL INDUSTRIAL CO., LTD.)), and the like. Phosphoric acid and sulfuric acid are preferably used.

The content of the acid component in the present solid formulation is an amount required to have a pH at 25° C. of a mixture of 1 g of the solid formulation and 99 g of ion exchange water of 8 or less, and can be determined depending on the type of the acid component and the targeted pH, and is usually 0.01 to 25% by weight, and preferably 0.01 to 15% by weight, as a total amount, based on 100% by weight of the present solid formulation. The acid component content of the present solid formulation can be determined, for example, by preparing a solid formulation using a prescribed amount of the acid component, together with other components by the method set forth below, measuring the pH by the above method, and adjusting the amount of the acid component based on the difference from the targeted pH, or the like.

The present solid formulation may further comprise lignin sulfonate. Examples of the lignin sulfonate used in the present invention include sodium salts, potassium salts and ammonium salts of lignin sulfonic acid. As the lignin sulfonate, lignin sulfonate having a weight average molecular weight of 3000 to 14000, a pH of 8 or less, and a sulfonation degree of 1.0 to 3.0 is preferable. The pH of the lignin sulfonate refers to the pH at 25° C. of a 15% (w/v) aqueous solution obtained by dissolving lignin sulfonate in ion exchange water. In the present invention, % (w/v) means a weight/volume percent concentration, and a 15% (w/v) aqueous solution refers to an aqueous solution in which the weight of lignin sulfonate dissolved in 100 mL of aqueous lignin sulfonate solution is 15 g. The pH of the lignin sulfonate can be measured by preparing a 15% (w/v) aqueous solution of lignin sulfonate, and measuring it in the same manner as in the case for the pH of the present solid formulation. Also, the sulfonation degree of the lignin sulfonate is the average number of sulfonic acid groups in one unit, when the molecular weight of one unit of lignin is 1000.

The lignin sulfonate having a weight average molecular weight of 3000 to 14000, a pH of 8 or less, and a sulfonation degree of 1.0 to 3.0 specifically includes Reax 80D (manufactured by MeadWestvaco Corporation, sodium lignin sulfonate having a pH at 25° C. of a 15% (w/v) aqueous solution of 7.0), Reax 88A (manufactured by MeadWestvaco Corporation, sodium lignin sulfonate having a pH at 25° C. of a 15% (w/v) aqueous solution of 4.3), Reax 907 (manufactured by MeadWestvaco Corporation, sodium lignin sulfonate having a pH at 25° C. of a 15% (w/v) aqueous solution of 7.2), and Reax 910 (manufactured by MeadWestvaco Corporation, sodium lignin sulfonate having a pH at 25° C. of a 15% (w/v) aqueous solution of 7.2), and the like.

When the present solid formulation comprises lignin sulfonate, the total content is usually 1 to 80% by weight, and preferably 20 to 50% by weight, based on 100% by weight of the present solid formulation.

The present solid formulation may further comprise an agrochemical adjuvant used in the normal agrochemical solid formulation. The agrochemical adjuvant includes solid carriers, surfactants, binders, antifoaming agents, and the like.

Examples of the solid carriers include mineral carriers such as kaolin clay, diatomaceous earth, agalmatolite, silica stone, bentonite, acid clay, activated clay, attapulgite clay, pyrophyllite, sericite, zeolite, zeeklite, wollastonite, calcium silicate, talc, pumice stone and white carbon; ammonium salts such as ammonium sulfate and ammonium chloride, phosphates such as potassium dihydrogen phosphate and dipotassium hydrogen phosphate, carbonates such as sodium carbonate, sodium hydrogen carbonate and calcium carbonate, saccharides such as glucose, fructose, sucrose, lactose and dextrin; and water soluble carriers such as urea, salt, sodium sulfate and polyethylene glycol that is solid at ordinary temperature.

The present solid formulation comprises the solid carrier in an amount of usually 0 to 30% by weight, and preferably 0 to 20% by weight, as a total amount, based on 100% by weight of the present solid formulation.

The surfactants include nonionic surfactants, anionic surfactants, cationic surfactants, ampholytic surfactants and mixtures thereof. Usually, a nonionic surfactant and/or an anionic surfactant is used. Examples of the nonionic surfactant include polyoxyethylene carboxylic acid ester, polyoxyethylene polyoxypropylene alkyl aryl ether, polyoxyethylene polyoxypropylene block copolymer, polyoxyethylene alkyl aryl ether, polyoxyethylene alkyl ether, polyoxyethylene polyoxypropylene tristyrylphenyl ether, polyoxyethylene styrylphenyl ether, polyoxyethylene tristyrylphenyl ether, polyoxyethylene fatty acid ester, fatty acid ester, polyhydric alcohol fatty acid ester, polyoxyethylene polyhydric alcohol fatty acid ester, and polyoxyethylene alkylamine. Also, examples of the anionic surfactant include dialkylsulfocarboxylic acid ester salt, alkyl sulfonate, alkyl aryl sulfonate, polycarboxylate, polyoxyethylene alkyl aryl ether phosphoric acid ester salt, polyoxyethylene tristyrylphenyl ether phosphoric acid ester salt, alkylnaphthalenesulfonate, naphthalenesulfonic acid polycondensate metal salt, alkenyl sulfonate, a salt of condensate of naphthalenesulfonic acid with formalin, dialkylsulfosuccinate, and alkylsulfate sodium salt.

The present solid formulation comprises the surfactant in an amount of usually 2 to 20% by weight, and preferably 4 to 10% by weight, as a total amount, based on 100% by weight of the present solid formulation.

As the binder, a water-soluble binder is preferred, and examples thereof include dextrin, polyvinyl alcohol, gum arabic, sodium alginate, polyvinylpyrrolidone, mannitol, and sorbitol.

The present solid formulation comprises the binder in an amount of usually 0 to 20% by weight, and preferably 0 to 10% by weight, as a total amount, based on 100% by weight of the present solid formulation.

As the antifoaming agent, a silicone-based antifoaming agent is preferred.

The present solid formulation comprises the antifoaming agent in an amount of usually 0 to 5% by weight, and preferably 0 to 3% by weight, as a total amount, based on 100% by weight of the present solid formulation.

Some examples of the present solid formulation are shown below. Here, the amount shows a weight based on the total weight of the present solid formulation.

An agrochemical solid formulation comprising 5 to 90% by weight of fenpyrazamine and 0.01 to 25% by weight of an acid component, and having a pH of the present solid formulation of 8 or less.

An agrochemical solid formulation comprising 5 to 90% by weight of fenpyrazamine and 0.01 to 25% by weight of an acid component, and having a pH of the present solid formulation of 3 or more and 8 or less.

An agrochemical solid formulation comprising 5 to 90% by weight of fenpyrazamine and 0.01 to 25% by weight of an acid component, and having a pH of the present solid formulation of 3 or more and 6 or less.

An agrochemical solid formulation comprising 5 to 90% by weight of fenpyrazamine and 0.01 to 15% by weight of phosphoric acid, and having a pH of the present solid formulation of 8 or less.

An agrochemical solid formulation comprising 5 to 90% by weight of fenpyrazamine and 0.01 to 15% by weight of phosphoric acid, and having a pH of the present solid formulation of 3 or more and 8 or less.

An agrochemical solid formulation comprising 5 to 90% by weight of fenpyrazamine and 0.01 to 15% by weight of phosphoric acid, and having a pH of the present solid formulation of 3 or more and 6 or less.

An agrochemical solid formulation comprising 5 to 90% by weight of fenpyrazamine, 0.01 to 25% by weight of an acid component and 1 to 80% by weight of lignin sulfonate, and having a pH of the present solid formulation of 8 or less.

An agrochemical solid formulation comprising 5 to 90% by weight of fenpyrazamine, 0.01 to 25% by weight of an acid component and 1 to 80% by weight of lignin sulfonate, and having a pH of the present solid formulation of 3 or more and 8 or less.

An agrochemical solid formulation comprising 5 to 90% by weight of fenpyrazamine, 0.01 to 25% by weight of an acid component and 1 to 80% by weight of lignin sulfonate, and having a pH of the present solid formulation of 3 or more and 6 or less.

An agrochemical solid formulation comprising 5 to 90% by weight of fenpyrazamine, 0.01 to 15% by weight of phosphoric acid and 1 to 80% by weight of lignin sulfonate, and having a pH of the present solid formulation of 8 or less.

An agrochemical solid formulation comprising 5 to 90% by weight of fenpyrazamine, 0.01 to 15% by weight of phosphoric acid and 1 to 80% by weight of lignin sulfonate, and having a pH of the present solid formulation of 3 or more and 8 or less.

An agrochemical solid formulation comprising 5 to 90% by weight of fenpyrazamine, 0.01 to 15% by weight of phosphoric acid and 1 to 80% by weight of lignin sulfonate, and having a pH of the present solid formulation of 3 or more and 6 or less.

An agrochemical solid formulation comprising 40 to 60% by weight of fenpyrazamine and 0.01 to 15% by weight of a phosphoric acid, and having a pH of the present solid formulation of 3 or more and 8 or less.

An agrochemical solid formulation comprising 40 to 60% by weight of fenpyrazamine, 0.01 to 15% by weight of phosphoric acid and 25 to 45% by weight of lignin sulfonate, and having a pH of the present solid formulation of 3 or more and 8 or less.

An agrochemical solid formulation comprising 40 to 60% by weight of fenpyrazamine, 0.01 to 15% by weight of phosphoric acid and 25 to 45% by weight of lignin sulfonate having a weight average molecular weight of 3000 to 14000, a pH of 8 or less and a sulfonation degree of 1.0 to 3.0, and having a pH of the present solid formulation of 3 or more and 8 or less.

An agrochemical solid formulation comprising 40 to 60% by weight of fenpyrazamine and 0.01 to 15% by weight of a phosphoric acid, and having a pH of the present solid formulation of 3 or more and 6 or less.

An agrochemical solid formulation comprising 40 to 60% by weight of fenpyrazamine, 0.01 to 15% by weight of phosphoric acid and 25 to 45% by weight of lignin sulfonate, and having a pH of the present solid formulation of 3 or more and 6 or less.

An agrochemical solid formulation comprising 40 to 60% by weight of fenpyrazamine, 0.01 to 15% by weight of phosphoric acid and 25 to 45% by weight of lignin sulfonate having a weight average molecular weight of 3000 to 14000, a pH of 8 or less and a sulfonation degree of 1.0 to 3.0, and having a pH of the present solid formulation of 3 or more and 6 or less.

The present solid formulation can be produced by mixing fenpyrazamine and an acid component in an amount required for having a pH of the present solid formulation of 8 or less (hereinafter referred to as Acid Component A), and as necessary, lignin sulfonate and an agrochemical adjuvant. The form (formulation type) of the present solid formulation is a wettable powder or a water dispersible granule, and a water dispersible granule is preferred from the viewpoint of protecting users. These formulations can be prepared by a known method.

The present solid formulation that is a water dispersible granule (hereinafter referred to as the present water dispersible granule) can be produced, for example, according to the following method.

A method for spraying an aqueous suspension comprising fenpyrazamine, Acid Component A and water, and as necessary, lignin sulfonate, a surfactant, a solid carrier, an antifoaming agent and the like, and drying it.

In this method, the aqueous suspension to be spray-dried can be prepared, for example, by the following method 1) or 2).

1) Fenpyrazamine, and as necessary, lignin sulfonate, a solid carrier, an antifoaming agent and the like are added to a prescribed amount of water (optionally containing a surfactant), and wet-pulverized using a wet pulverizer such as a horizontal bead mill, a sand grinder or the like. Acid Component A may be added before pulverization, or added after pulverization.

2) Fenpyrazamine, and as necessary, a solid carrier and the like are homogeneously mixed using a mixer such as a ribbon mixer, a juice blender or a Nauta mixer, and then dry-pulverized using a pulverizer such as a hammer mill, a pin mill, a jet mill or a centrifugal pulverizer. The pulverized mixture is again mixed using a mixer as the case may be, then the pulverized mixture, and lignin sulfonate as necessary, are added to a prescribed amount of water (optionally containing a surfactant), an antifoaming agent and the like are further added as necessary, and the mixture is homogeneously suspended using a stirrer such as a disperser. Acid Component A may be mixed with fenpyrazamine before dry pulverization, but is usually added to water together with the pulverized mixture containing fenpyrazamine after dry pulverization.

In the wet pulverization or dry pulverization for preparing the above aqueous suspension, pulverization is performed so that the particle size of fenpyrazamine in the aqueous suspension may be 0.5 to 20 μm and preferably 1 to 15 μm. In the present invention, the particle size of fenpyrazamine means a volume median diameter of crystals of fenpyrazamine. The volume median diameter refers to a particle diameter at which a cumulative frequency in a volume-based frequency distribution is to be 50%, and can be obtained, for example, by wet measurement using a laser diffraction particle size distribution measuring apparatus. More specifically, the crystals of fenpyrazamine are dispersed in water, and the volume median diameter is measured using the apparatus. Examples of the laser diffraction particle size distribution measuring apparatus include Mastersizer 2000 (manufactured by Malvern Instruments Ltd).

Spray-drying is performed, for example, by bringing an aqueous suspension sprayed from a pressure spray nozzle or a rotary atomizer into contact with hot air. In the spray-drying, conditions such as the feed amount (feed flow rate) of the aqueous suspension from the pressure spray nozzle or the rotary atomizer, spray-drying temperature, the hot air supply quantity, direction of hot air and the like are properly adjusted, whereby the particle size of the present water dispersible granule to be obtained can be controlled. Usually, the above conditions are adjusted so that the outlet temperature may be 80° C. or less and the temperature of the present water dispersible granule immediately after drying may be 90° C. or less. Also, the conditions of spray-drying are adjusted so that the particle size of the present water dispersible granule to be obtained usually may be 0.1 to 1 mm. In the present invention, the particle size of the present water dispersible granule means a volume median diameter of the present water dispersible granule. The volume median diameter refers to a particle diameter at which a cumulative frequency in a volume-based frequency distribution is to be 50%, and can be obtained, for example, by dry measurement using a laser diffraction particle size distribution measuring apparatus. More specifically, the present water dispersible granule is dispersed in the air, and the volume median diameter is measured using the apparatus. Examples of the laser diffraction particle size distribution measuring apparatus include Mastersizer 2000 (manufactured by Malvern Instruments Ltd).

The present method also includes a method in which primary particles sprayed and dried to some extent are subjected to further granulation in a fluidized bed, namely, a method in which an aqueous suspension comprising fenpyrazamine, Acid Component A and water, and as necessary, lignin sulfonate, a surfactant, a solid carrier, an antifoaming agent and the like is sprayed in a fluidized bed apparatus, continuously performing the fluidized bed granulation following the spray granulation (for example, FSD technology of GEA NIRO).

In the method, the aqueous suspension to be spray-dried in the fluidized bed can be prepared, for example, by the above method 1) or 2).

In the wet pulverization or dry pulverization for preparing the above aqueous suspension, pulverization is performed so that the particle size of fenpyrazamine in the aqueous suspension may be 0.5 to 20 µm and preferably 1 to 15 µm.

The obtained aqueous suspension is sprayed in the fluidized bed from the top (top spray) or bottom (bottom spray) of the apparatus, for example, using a pressure spray nozzle or a rotary atomizer, and contact flocculation occurs when spray mist is contacted with hot air in the fluidized bed and dried, thereby forming a granular matter larger than the primary particles immediately after spraying. The primary particle size and the secondary particle size after flocculation of the granular matter (the present water dispersible granule) obtained by adjusting conditions such as the feed amount (feed flow rate) of the aqueous suspension from the pressure spray nozzle or the rotary atomizer, drying temperature in the fluidized bed, the hot air supply quantity, direction of hot air and the like can be controlled. Usually, the secondary particle size after flocculation is controlled by adjusting the dry state in the fluidized bed. Specifically, humidity in the bed becomes high under such conditions that feed flow rate/(drying temperature×hot air supply quantity) becomes large, and the secondary particle size of the present water dispersible granule becomes large. On the other hand, humidity in the bed becomes low under such conditions that feed flow rate/(drying temperature×hot air supply quantity) becomes small, and the secondary particle size of the present water dispersible granule becomes small. Usually, during the production, each condition is adjusted so that the temperature of the present water dispersible granule immediately after drying may be 30 to 90° C. In the present invention, each condition is adjusted so that the particle size (secondary particle size) of the present water dispersible granule to be obtained usually may be 0.1 to 3 mm, and preferably 0.1 to 1 mm.

In the present invention, the amount of the present water dispersible granule as the standard of the amount of each component contained in the present water dispersible granule does not contain moisture remaining during drying after granulation or moisture increased by moisture absorption after storage.

EXAMPLES

The present invention will be described in further detail below by way of Examples.

First, production examples and comparative production examples will be shown.

Production Example 1

Fenpyrazamine (purity of 97% by weight) was dry-pulverized by a vertical jet mill (JOM-0101 model jet crusher, manufactured by Seishin Enterprise Co., Ltd.), and fenpyrazamine fine powder having a particle size of fenpyrazamine of 2.7 µm was prepared.

51.5 Parts by weight of the resulting fenpyrazamine fine powder, 5 parts by weight of potassium polycarboxylate (Geropon SC/213, manufactured by Rhodia), 42.6 parts by weight of sodium lignin sulfonate (Reax 85A, manufactured by MeadWestvaco Corporation), 0.9 parts by weight of phosphoric acid and 300 parts by weight of ion exchange water were mixed until the mixture became uniform to obtain an aqueous suspension. The aqueous suspension was spray-dried using a spray dryer (model SD-1, manufactured by TOKYO RIKAKIKAI CO, LTD) to obtain Present Agrochemical Solid Formulation (1).

The pH at 25° C. of a mixed liquid of 1 g of Present Agrochemical Solid Formulation (1) and 99 g of ion exchange water was 8.1.

Production Example 2

51.5 Parts by weight of the fenpyrazamine fine powder prepared in Production Example 1, 5 parts by weight of potassium polycarboxylate (Geropon SC/213, manufactured by Rhodia), 41.3 parts by weight of sodium lignin sulfonate (Reax 85A, manufactured by MeadWestvaco Corporation), 2.2 parts by weight of phosphoric acid and 300 parts by weight of ion exchange water were mixed until the mixture became uniform to obtain an aqueous suspension. The aqueous suspension was spray-dried using a spray dryer (model SD-1, manufactured by TOKYO RIKAKIKAI CO, LTD) to obtain Present Agrochemical Solid Formulation (2).

The pH at 25° C. of a mixed liquid of 1 g of Present Agrochemical Solid Formulation (2) and 99 g of ion exchange water was 6.7.

Production Example 3

51.5 Parts by weight of the fenpyrazamine fine powder prepared in Production Example 1, 5 parts by weight of potassium polycarboxylate (Geropon SC/213, manufactured by Rhodia), 39.1 parts by weight of sodium lignin sulfonate (Reax 85A, manufactured by MeadWestvaco Corporation), 4.4 parts by weight of phosphoric acid and 300 parts by weight of ion exchange water were mixed until the mixture became uniform to obtain an aqueous suspension. The aqueous suspension was spray-dried using a spray dryer (model SD-1, manufactured by TOKYO RIKAKIKAI CO, LTD) to obtain Present Agrochemical Solid Formulation (3).

The pH at 25° C. of a mixed liquid of 1 g of Present Agrochemical Solid Formulation (3) and 99 g of ion exchange water was 5.7.

Production Example 4

51.5 Parts by weight of the fenpyrazamine fine powder prepared in Production Example 1, 5 parts by weight of potassium polycarboxylate (Geropon SC/213, manufactured by Rhodia), 38.3 parts by weight of sodium lignin sulfonate (Reax 85A, manufactured by MeadWestvaco Corporation), 5.2 parts by weight of phosphoric acid and 300 parts by weight of ion exchange water were mixed until the mixture became uniform to obtain an aqueous suspension. The aqueous suspension was spray-dried using a spray dryer (model SD-1, manufactured by TOKYO RIKAKIKAI CO, LTD) to obtain Present Agrochemical Solid Formulation (4).

The pH at 25° C. of a mixed liquid of 1 g of Present Agrochemical Solid Formulation (4) and 99 g of ion exchange water was 5.0.

Production Example 5

51.5 Parts by weight of the fenpyrazamine fine powder prepared in Production Example 1, 5 parts by weight of potassium polycarboxylate (Geropon SC/213, manufactured by Rhodia), 36.6 parts by weight of sodium lignin sulfonate (Reax 85A, manufactured by MeadWestvaco Corporation), 6.9 parts by weight of phosphoric acid and 300 parts by weight of ion exchange water were mixed until the mixture became uniform to obtain an aqueous suspension. The aqueous suspension was spray-dried using a spray dryer (model SD-1, manufactured by TOKYO RIKAKIKAI CO, LTD) to obtain Present Agrochemical Solid Formulation (5).

The pH at 25° C. of a mixed liquid of 1 g of Present Agrochemical Solid Formulation (5) and 99 g of ion exchange water was 4.0.

Production Example 6

51.5 Parts by weight of the fenpyrazamine fine powder prepared in Production Example 1, 5 parts by weight of potassium polycarboxylate (Geropon SC/213, manufactured by Rhodia), 30.7 parts by weight of sodium lignin sulfonate (Reax 85A, manufactured by MeadWestvaco Corporation), 12.8 parts by weight of phosphoric acid and 300 parts by weight of ion exchange water were mixed until the mixture became uniform to obtain an aqueous suspension. The aqueous suspension was spray-dried using a spray dryer (model SD-1, manufactured by TOKYO RIKAKIKAI CO, LTD) to obtain Present Agrochemical Solid Formulation (6).

The pH at 25° C. of a mixed liquid of 1 g of Present Agrochemical Solid Formulation (6) and 99 g of ion exchange water was 2.5.

Production Example 7

77.3 Parts by weight of the fenpyrazamine fine powder prepared in Production Example 1, 5.0 parts by weight of potassium polycarboxylate (Geropon SC/213, manufactured by Rhodia), 17.2 parts by weight of sodium lignin sulfonate (Reax 85A, manufactured by MeadWestvaco Corporation) and 0.5 parts by weight of a 10% aqueous phosphoric acid solution were stirred and mixed using a juice blender to obtain Present Agrochemical Solid Formulation (7).

The pH at 25° C. of a mixed liquid of 1 g of Present Agrochemical Solid Formulation (7) and 99 g of ion exchange water was 8.3.

Production Example 8

77.3 Parts by weight of the fenpyrazamine fine powder prepared in Production Example 1, 5.0 parts by weight of potassium polycarboxylate (Geropon SC/213, manufactured by Rhodia), 16.7 parts by weight of sodium lignin sulfonate (Reax 85A, manufactured by MeadWestvaco Corporation) and 1.0 parts by weight of a 10% aqueous phosphoric acid solution were stirred and mixed using a juice blender to obtain Present Agrochemical Solid Formulation (8).

The pH at 25° C. of a mixed liquid of 1 g of Present Agrochemical Solid Formulation (8) and 99 g of ion exchange water was 6.7.

Production Example 9

77.3 Parts by weight of the fenpyrazamine fine powder prepared in Production Example 1, 5.0 parts by weight of potassium polycarboxylate (Geropon SC/213, manufactured by Rhodia), 15.6 parts by weight of sodium lignin sulfonate (Reax 85A, manufactured by MeadWestvaco Corporation) and 2.1 parts by weight of a 10% aqueous phosphoric acid solution were stirred and mixed using a juice blender to obtain Present Agrochemical Solid Formulation (9).

The pH at 25° C. of a mixed liquid of 1 g of Present Agrochemical Solid Formulation (9) and 99 g of ion exchange water was 6.3.

Production Example 10

77.3 Parts by weight of the fenpyrazamine fine powder prepared in Production Example 1, 5.0 parts by weight of potassium polycarboxylate (Geropon SC/213, manufactured by Rhodia), 14.1 parts by weight of sodium lignin sulfonate (Reax 85A, manufactured by MeadWestvaco Corporation) and 3.6 parts by weight of a 10% aqueous phosphoric acid solution were stirred and mixed using a juice blender to obtain Present Agrochemical Solid Formulation (10).

The pH at 25° C. of a mixed liquid of 1 g of Present Agrochemical Solid Formulation (10) and 99 g of ion exchange water was 5.4.

Production Example 11

77.3 Parts by weight of the fenpyrazamine fine powder prepared in Production Example 1, 5.0 parts by weight of potassium polycarboxylate (Geropon SC/213, manufactured by Rhodia), 13.1 parts by weight of sodium lignin sulfonate (Reax 85A, manufactured by MeadWestvaco Corporation) and 4.7 parts by weight of a 10% aqueous phosphoric acid solution were stirred and mixed using a juice blender to obtain Present Agrochemical Solid Formulation (11).

The pH at 25° C. of a mixed liquid of 1 g of Present Agrochemical Solid Formulation (11) and 99 g of ion exchange water was 4.7.

Production Example 12

77.3 Parts by weight of the fenpyrazamine fine powder prepared in Production Example 1, 5.0 parts by weight of potassium polycarboxylate (Geropon SC/213, manufactured by Rhodia), 10.4 parts by weight of sodium lignin sulfonate (Reax 85A, manufactured by MeadWestvaco Corporation) and 7.3 parts by weight of a 10% aqueous phosphoric acid solution were stirred and mixed using a juice blender to obtain Present Agrochemical Solid Formulation (12).

The pH at 25° C. of a mixed liquid of 1 g of Present Agrochemical Solid Formulation (12) and 99 g of ion exchange water was 3.0.

Production Example 13

51.2 Parts by weight of fenpyrazamine, 5 parts by weight of potassium polycarboxylate (Geropon SC/213, manufactured by Rhodia), 37.29 parts by weight of sodium lignin sulfonate (Reax 80D, manufactured by MeadWestvaco Corporation), 0.01 parts by weight of phosphoric acid, 0.5 parts by weight of a mixture of a self-emulsifiable silicone-based antifoaming agent (KS-530, manufactured by Shin-Etsu Chemical Co., Ltd.) and ion exchange water (weight ratio 1:4) and 117 parts by weight of ion exchange water are mixed, and then wet-pulverized using a horizontal bead mill (trade name: DYNO-MILL KDL, manufactured by SHIN-MARU ENTERPRISES CORPORATION) to obtain a fenpyrazamine suspension. On the other hand, 4 parts by weight of potassium dihydrogen phosphate is dissolved in 23 parts by weight of ion exchange water to obtain an aqueous potassium dihydrogen phosphate solution. The aqueous potassium dihydrogen phosphate solution and 12 parts by weight of the mixture of a self-emulsifiable silicone-based antifoaming agent (trade name: KS-530, manufactured by Shin-Etsu Chemical Co., Ltd.) and ion exchange water (weight ratio 1:4) are mixed to the fenpyrazamine suspension to obtain an aqueous suspension. The aqueous suspension is spray-dried using a fluidized bed granulating machine (STREA-1, manufactured by Powrex Corporation) and granulated by a method of continuously performing the fluidized bed granulation following the spray granulation to obtain an agrochemical solid formulation.

The conditions during the production are shown below.
feed flow rate: 5 g/min at start, 25 g/min at steady state
Drying temperature: 90° C. at start, 80° C. at steady state
Hot air supply quantity: 85 m³/h at start, 50 m³/h at steady state The pH at 25° C. of a mixed liquid of 1 g of the obtained agrochemical solid formulation and 99 g of ion exchange water is 8 or less.

Comparative Production Example 1

51.5 Parts by weight of the fenpyrazamine fine powder prepared in Production Example 1, 5 parts by weight of potassium polycarboxylate (Geropon SC/213, manufactured by Rhodia), 43.5 parts by weight of sodium lignin sulfonate (Reax 85A, manufactured by MeadWestvaco Corporation) and 300 parts by weight of ion exchange water were mixed until the mixture became uniform to obtain an aqueous suspension. The aqueous suspension was spray-dried using a spray dryer (model SD-1, manufactured by TOKYO RIKAKIKAI CO, LTD) to obtain Comparative Agrochemical Solid Formulation (1).

The pH at 25° C. of a mixed liquid of 1 g of Comparative Agrochemical Solid Formulation (1) and 99 g of ion exchange water was 9.8.

Comparative Production Example 2

77.3 Parts by weight of the fenpyrazamine fine powder prepared in Production Example 1, 5.0 parts by weight of potassium polycarboxylate (Geropon SC/213, manufactured by Rhodia) and 17.7 parts by weight of sodium lignin sulfonate (Reax 85A, manufactured by MeadWestvaco Corporation) were stirred and mixed using a juice blender to obtain Comparative Agrochemical Solid Formulation (2).

The pH at 25° C. of a mixed liquid of 1 g of Present Comparative Agrochemical Solid Formulation (2) and 99 g of ion exchange water was 10.0.

Next, a test example will be shown.

Test Example 1

Each 10 g of Present Agrochemical Solid Formulations (1) to (12) and Comparative Agrochemical Solid Formulations (1) to (2) was put in an aluminum bag and sealed, and they were left in a thermostat at 54° C. for 2 weeks. Thereafter, as to each agrochemical solid formulation, sensory test of the odor derived from fenpyrazamine was performed by three panelists, based on the following determination criteria. The average value of the determination values of three panelists was calculated. The result is shown in Table 1.

Determination Criteria
0: There is no odor
1: There is odor
2: There is strong odor
3: There is very strong odor Odor between 0 and 1, odor between 1 and 2 and odor between 2 and 3 were determined as 0.5, 1.5 and 2.5, respectively.

TABLE 1

| Tested agrochemical solid formulation | Odor after 2 weeks storage at 54° C. |
|---|---|
| Present Agrochemical Solid Formulation (1) | 1.0 |
| Present Agrochemical Solid Formulation (2) | 0.5 |
| Present Agrochemical Solid Formulation (3) | 0.0 |
| Present Agrochemical Solid Formulation (4) | 0.0 |
| Present Agrochemical Solid Formulation (5) | 0.0 |
| Present Agrochemical Solid Formulation (6) | 0.0 |
| Present Agrochemical Solid Formulation (7) | 1.8 |
| Present Agrochemical Solid Formulation (8) | 1.3 |
| Present Agrochemical Solid Formulation (9) | 0.5 |
| Present Agrochemical Solid Formulation (10) | 0.5 |
| Present Agrochemical Solid Formulation (11) | 0.5 |
| Present Agrochemical Solid Formulation (12) | 1.0 |
| Comparative Agrochemical Solid Formulation (1) | 2.0 |
| Comparative Agrochemical Solid Formulation (2) | 2.3 |

The invention claimed is:

1. An agrochemical solid formulation comprising 5 to 90% by weight of fenpyrazamine and 0.01 to 15% by weight of an acid based on 100% by weight of the agrochemical solid formulation, wherein the pH at 25° C. of a mixture of 1 g of the agrochemical solid formulation and 99 g of ion exchange water is 8 or less, and wherein the agrochemical solid formulation is a wettable powder or a water dispersible granule.

2. The agrochemical solid formulation according to claim 1, wherein the acid is at least one selected from the group consisting of phosphoric acid and sulfuric acid.

3. The agrochemical solid formulation according to claim 1, wherein the pH is in a range of 3 to 6.

4. The agrochemical solid formulation according to claim 1, further comprising lignin sulfonate.

5. The agrochemical solid formulation according to claim 2, wherein the pH is in a range of 3 to 6.

6. The agrochemical solid formulation according to claim 2, further comprising lignin sulfonate.

7. The agrochemical solid formulation according to claim 3, further comprising lignin sulfonate.

8. The agrochemical solid formulation according to claim 1, wherein the acid is an inorganic acid or an organic acid.

9. The agrochemical solid formulation according to claim 1, wherein the acid is an inorganic acid.

10. The agrochemical solid formulation according to claim 1, wherein the agrochemical solid formulation is a water dispersible granule.

* * * * *